United States Patent
Slepian et al.

(10) Patent No.: US 11,458,470 B2
(45) Date of Patent: Oct. 4, 2022

(54) SYSTEMS AND METHODS FOR ANALYZING PLATELET FUNCTION

(71) Applicants: ARIZONA BOARD OF REGENTS ON BEHALF OF THE UNIVERSITY OF ARIZONA, Tucson, AZ (US); POLITECNICO DI MILANO, Milan (IT)

(72) Inventors: Marvin Slepian, Tucson, AZ (US); Alberto Redaelli, Milan (IT)

(73) Assignees: ARIZONA BOARD OF REGENTS ON BEHALF OF THE UNIVERSITY OF ARIZONA, Tucson, AZ (US); POLITECNICO DI MILANO

( * ) Notice: Subject to any disclaimer, the term of this patent is extended or adjusted under 35 U.S.C. 154(b) by 126 days.

(21) Appl. No.: 16/624,112

(22) PCT Filed: Jun. 22, 2018

(86) PCT No.: PCT/US2018/038955
§ 371 (c)(1),
(2) Date: Dec. 18, 2019

(87) PCT Pub. No.: WO2018/237246
PCT Pub. Date: Dec. 27, 2018

(65) Prior Publication Data
US 2020/0206733 A1 Jul. 2, 2020

Related U.S. Application Data

(60) Provisional application No. 62/524,243, filed on Jun. 23, 2017.

(51) Int. Cl.
*B01L 3/00* (2006.01)
*G01N 33/86* (2006.01)

(52) U.S. Cl.
CPC ........ *B01L 3/502715* (2013.01); *G01N 33/86* (2013.01)

(58) Field of Classification Search
CPC .. B01L 3/502715; B01L 3/5027; B01L 3/502; B01L 3/50; G01N 33/86; G01N 33/50; G01N 33/48
(Continued)

(56) References Cited

U.S. PATENT DOCUMENTS 4,788,139 A * 11/1988 Ryan .................. G01N 33/86
435/13
5,380,491 A    1/1995 Carver, Jr. et al.
(Continued)

FOREIGN PATENT DOCUMENTS

WO    WO 2016/033455 A1 *  3/2016  ................ B01L 3/00

OTHER PUBLICATIONS

Choi, Jae-Lim, Shuhua Li, and Jin-Yeong Han. "Platelet function tests: a review of progresses in clinical application." BioMed research international May 2014, 7 pages.
(Continued)

*Primary Examiner* — Christine T Mui
(74) *Attorney, Agent, or Firm* — Casimir Jones, S.C.; Tanya A. Arenson

(57) ABSTRACT

Provided herein are devices, systems, and methods for analyzing platelet function. In particular, provided herein are simple, portable, accurate and inexpensive small footprint platelet aggregometry devices, systems, and methods.

19 Claims, 18 Drawing Sheets

(58) Field of Classification Search
USPC .......................... 436/69; 422/502, 501, 500
See application file for complete search history.

(56) References Cited

U.S. PATENT DOCUMENTS

| | | | |
|---|---|---|---|
| 6,169,394 B1 | 1/2001 | Frazier et al. | |
| 8,323,466 B2* | 12/2012 | Kim | H01L 29/0673 |
| | | | 204/403.01 |
| 8,702,922 B2* | 4/2014 | Asai | B01L 3/5085 |
| | | | 204/403.01 |
| 2006/0246528 A1* | 11/2006 | Swaim | G01N 33/86 |
| | | | 435/13 |
| 2010/0022755 A1* | 1/2010 | Umeda | C07K 14/78 |
| | | | 530/381 |
| 2010/0140110 A1* | 6/2010 | Kim | B82Y 10/00 |
| | | | 536/25.4 |
| 2015/0338424 A1 | 11/2015 | Shin et al. | |

OTHER PUBLICATIONS

International Search Report & Written Opinion, Int'l Patent Application No. PCT/US2018/038955, dated Sep. 19, 2018, 8 pages.

* cited by examiner

SYSTEMS AND METHODS FOR ANALYZING PLATELET FUNCTION

CROSS-REFERENCE TO RELATED APPLICATIONS

This application is a U.S. 371 national phase entry of International Patent Application No. PCT/US2018/038955, filed Jun. 22, 2018, which claims priority to and the benefit of U.S. Provisional Application No. 62/524,243, filed Jun. 23, 2017, each of which is hereby incorporated by reference in its entirety.

FIELD OF THE DISCLOSURE

Provided herein are devices, systems, and methods for analyzing platelet function. In particular, provided herein are simple, portable, accurate and inexpensive small footprint platelet aggregometry devices, systems, and methods.

BACKGROUND

Thrombosis or "clot formation" is a basic pathologic process that underlies many diseases including heart disease, stroke peripheral artery disease with, limb ischemia, pulmonary emboli, and malignancy related thrombosis. Heart disease in particular is the leading cause of death in the US and worldwide, accounting for >30% of deaths overall, with more than 50% of this mortality related to atherosclerotic coronary artery disease involving myocardial ischemia and infarction, all involving clot formation. Thrombus formation is understood to classically be driven by what is known as "Virchows Triad" —1. damaged vascular surfaces/endothelial dysfunction; 2. inflammatory blood; 3. altered blood flow. Central in all of these driving elements of clotting is the platelet. In the setting of vascular injury, atherosclerotic disease or inflammation platelets are activated via either inflammatory/chemical mediators or abnormal blood flow patterns beginning the process. As such platelets are initially activated and then aggregate leading to progressive clot formation, vessel occlusion tissue ischemia, infarction and ultimately death.

Today, platelet aggregation is the mainstay of tests utilized to assess platelet function, platelet activation and the response to antiplatelet pharmacologic agents, as a therapy to manipulate disease states with platelet-driven thrombosis. Traditional platelet aggregometry involves large, optical, laboratory-based instruments that are expensive, available in limited clinical laboratories, with tests not usually performed on a daily routine basis other than in tertiary medical centers. As such, while recognized to be a vital methodology to assess platelet function, aggregometry has had variable use and only "partial penetrance" into the market, despite its value. More recently a range of electronic aggregometry systems have been devised, which are an improvement over traditional optical systems, yet they remain large lab instruments.

What is needed is a simple device to assess platelet aggregation—both its onset and progression and degree of severity, to guide and provide warning signs of onset and progression of disease, response to antiplatelet (drug) therapy, which may be used both at the bedside and in the laboratory.

SUMMARY

The devices, systems, and methods described herein provide improved methods of performing platelet aggregometry. The devices described herein are small, rapid, and effective aggregation devices and systems that are highly portable. Such devices and systems find use both at the bedside or in the field, or even at home, and are inexpensive and accurate.

For example, in some embodiments, provides herein is a microfluidic device, comprising: an assay chamber comprising two electrodes that bridge the assay chamber; and a plurality of inflow channels in fluid communication with the assay chamber. In some embodiments, the plurality of inflow channels comprises two distinct channels. In some embodiments, the electrodes are not in operable communication with the plurality of inflow channels. In some embodiments, the electrodes are oriented perpendicular to the plurality of inflow channels. In some embodiments, the chamber is round, although other geometries may be utilized. In some embodiments, the plurality of inflow channels comprises two channels separated by 180 degrees. In some embodiments, the device is portable. In some embodiments, the electrodes and/or chamber is coated with a protein (e.g., fibrinogen, fibrin, collagens, vitronectin, or laminin).

Further embodiments provide a system, comprising: a) a device as described herein; and b) an analysis component configured to measure electrical impedance across the electrodes. In some embodiments, the analysis component comprises a computer processor and computer software and optionally a display component configured to display electrical impedance. In some embodiments, the system further comprises a platelet activation component. The present invention is not limited to particular platelet activation components. Examples include, but are not limited to, calcium chloride and an additional component selected from, for example, a device configured to deliver mechanical stimuli (e.g., a shearing device) and a platelet agonist (e.g., including but not limited to, arachidonic acid, thrombin, TRAP, adenine di-phosphate (ADP), epinephrine, collagen, or ristocetin).

Yet other embodiments provide a method of measuring platelet aggregometry, comprising: a) contacting a sample comprising blood or blood product comprising platelets with the chamber of a system as described herein; b) activating the platelets using the platelet activation component; and c) measuring electrical impedance across the electrodes. In some embodiments, the blood product is platelet rich plasma. In some embodiments, the sample is from a subject (e.g., a subject undergoing anti-coagulation therapy, a subject with heart disease, a subject undergoing a myocardial infarction, a subject with peripheral artery disease, a subject with limb ischemia, a subject with pulmonary emboli, or a subject with cancer). In some embodiments, the method further comprises the step of contacting the sample with a test compound (e.g., an anti-thrombotic, anti-platelet, anti-coagulation, thrombotic, platelet activating, or coagulation agent). In some embodiments, the contacting is in the chamber of the device. In some embodiments, the method is repeated over time on a subject undergoing treatment for a disease or condition. In some embodiments, the impedance results are used to determine or alter a treatment course of action (e.g., anti-coagulation therapy).

Still further embodiments provide the use of a system as described herein to measure platelet aggregometry or determine a treatment course of action in a blood or blood product comprising platelets sample from a subject.

Additional embodiments are described herein.

DEFINITIONS

The term "sample" in the present specification and claims is used in its broadest sense. It is meant to include both biological and environmental samples. A sample may include a specimen of synthetic origin.

Biological samples may be animal, including human, fluid, solid (e.g., stool), blood or blood products (e.g., platelet rich plasma) or tissue. Biological samples may be obtained from all of the various families of domestic animals, as well as feral or wild animals, including, but not limited to, such animals as ungulates, bear, fish, lagamorphs, rodents, etc.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, "microfluidic" refers to, for example, a device for transport or storage of small volumes (e.g., of liquids such as assay reagents). In some embodiments, individual channels or chamber of microfluidic devices comprise a volume of 10 nL to 1 µL (e.g., 10, 20, 50, 100, 200, 300, 400, 500, or 750 nL), although other sizes are contemplated.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present disclosure.

DETAILED DESCRIPTION

Provided herein are devices, systems, and methods for analyzing platelet function. In particular, provided herein are simple, portable, accurate and inexpensive small footprint platelet aggregometry devices, systems, and methods.

Platelet aggregometry involves a series of tests performed on whole blood or platelet-rich plasma, using several agonists (platelet activators) or mechanical activation. The agonist is added to the platelet sample and a dynamic measure of platelet clumping is recorded. Simultaneously to platelet aggregation, luminometry test can be performed. In that case, ATP release is assayed using a luminescent marker.

In some embodiments, provided herein is a simple, portable, accurate and inexpensive small footprint platelet aggregometry device and system, that at its core integrates microfluidics, electronics and impedance measurements. Exemplary devices are described below. Such devices find use in research, screening, and clinical applications.

I. Devices and Systems

Figure 1:
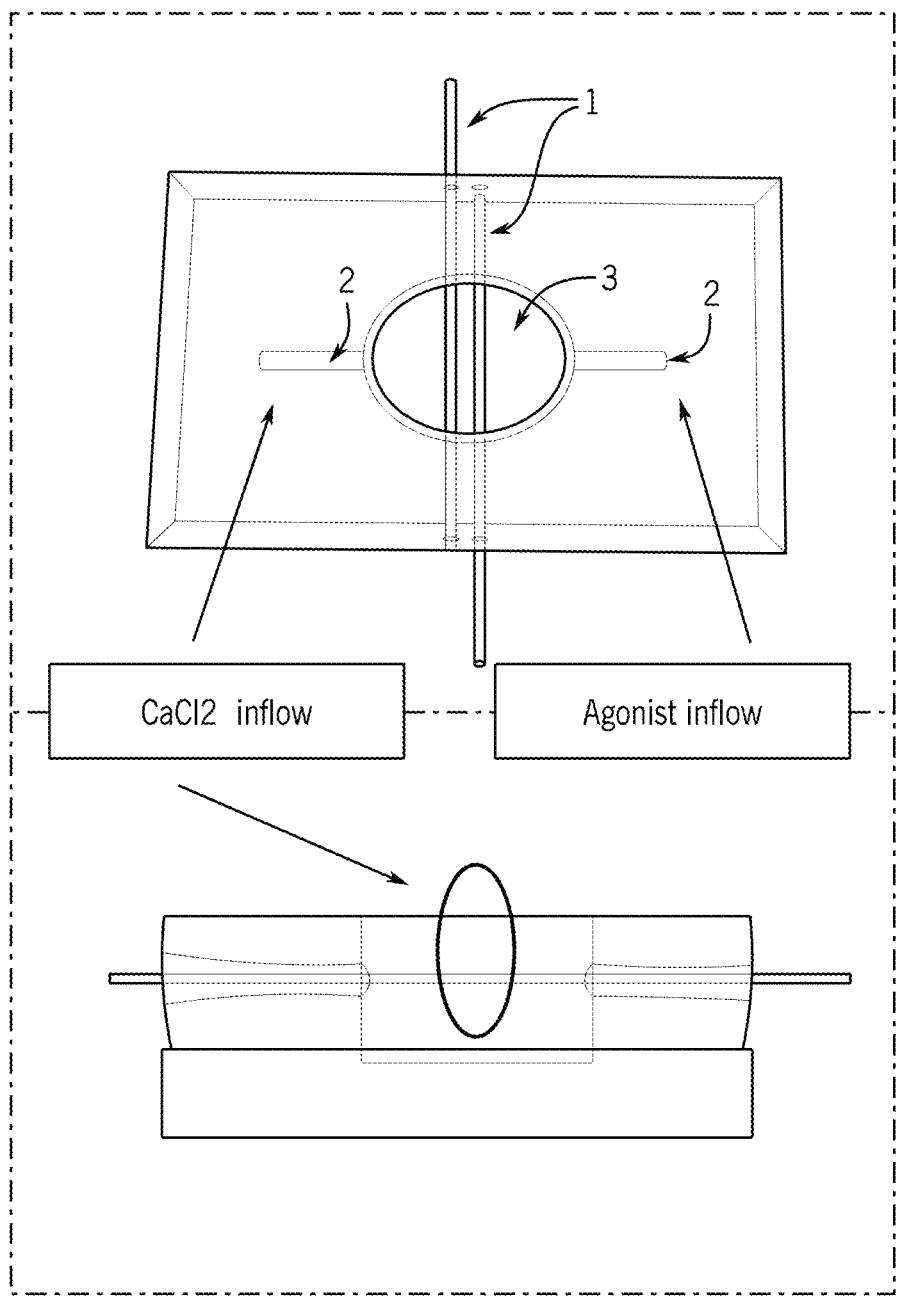
FIG. 1 shows top and lateral view of exemplary MICELI microfluidic chip devices.
Figure 2:
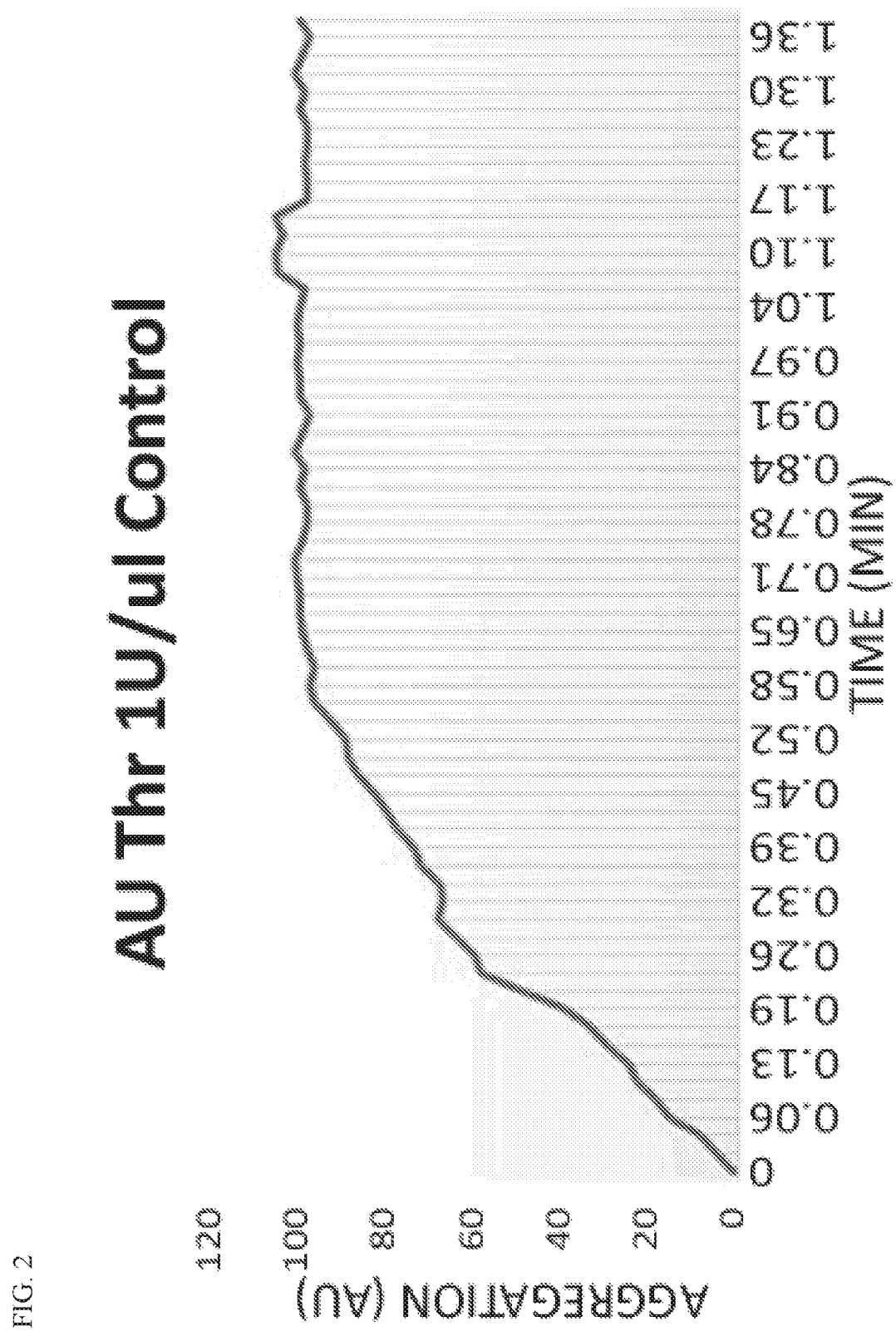
FIG. 2 shows Left: Aggregation (AU) curve MICELI; Right: Aggregation (AU) curve Multiplate system.
Figure 2:
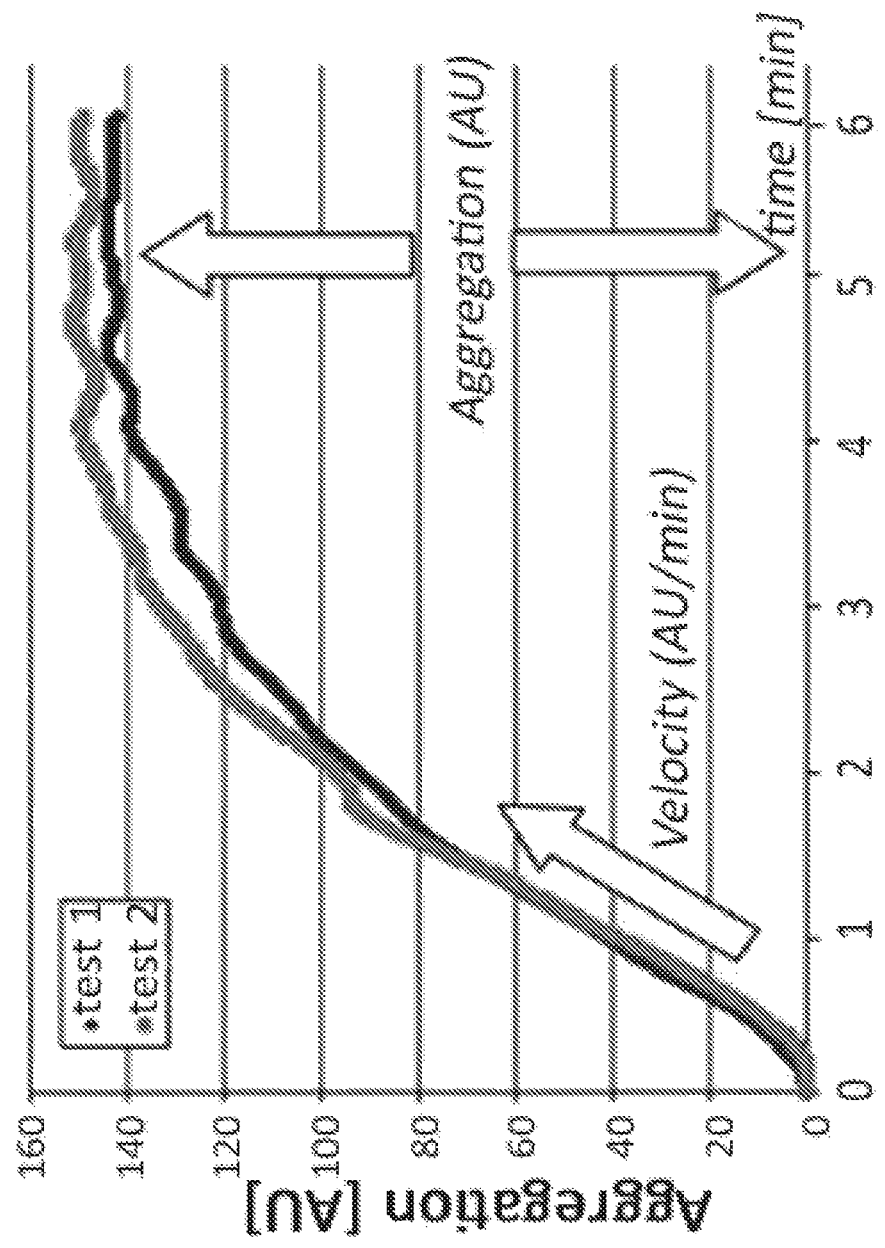

An exemplary device is described in FIG. 1. As shown in FIG. 1, in some embodiments, the microfluidic device comprises an assay chamber 3 comprising two electrodes 1 that bridge the assay chamber; and a plurality of inflow channels 2 in fluid communication with the assay chamber. In some embodiments, the plurality of inflow channels comprises two distinct channels. In some embodiments, the electrodes are not in operable communication with the plurality of inflow channels. In some embodiments, the electrodes are oriented perpendicular to the plurality of inflow channels. In some embodiments, the chamber is round, although other geometries may be utilized (e.g., square, oval, rectangular, etc.). In some embodiments, the plurality of inflow channels comprises two channels separated by 180 degrees. In some embodiments, the device is portable. In some embodiments, electrodes are functionalized with fibrils of collagen (e.g., to recruit platelet aggregates).

The microfluidic device is constructed of any suitable material. In some embodiments, layers are made by supplying a negative "master" and casting a castable material over the master. Castable materials include, but are not limited to, polymers, including epoxy resins, curable polyurethane elastomers, polymer solutions (e.g., solutions of acrylate polymers in methylene chloride or other solvents), curable polyorganosiloxanes, and polyorganosiloxanes which predominately bear methyl groups (e.g., polydimethylsiloxanes ("PDMS")). Curable PDMS polymers are available from many sources. Both addition curable and condensation-curable systems are available, as also are peroxide-cured systems. All these PDMS polymers have a small proportion of reactive groups which react to form crosslinks and/or cause chain extension during cure. Both one part (RTV-1) and two part (RTV-2) systems are available.

In some embodiments, transparent devices are desirable. Such devices may be made of glass or transparent polymers. PDMS polymers are well suited for transparent devices. A benefit of employing a polymer that is slightly elastomeric is the case of removal from the mold and the potential for providing undercut channels, which is generally not possible with hard, rigid materials. Methods of fabrication of microfluidic devices by casting of silicone polymers are well known. See, e.g. D. C. Duffy et al., "Rapid Prototyping of Microfluidic Systems in Poly(dimethylsiloxane)," Analytical Chemistry 70, 4974-4984 (1998). See also, J. R. Anderson et al., Analytical Chemistry 72, 3158-64 (2000); and M. A. Unger et al., Science 288, 113-16 (2000), each of which is herein incorporated by reference in its entirety.

In some embodiments, fluids are supplied to the device by any suitable method. Fluids may, for example, be supplied from syringes, from microtubing attached to or bonded to the inlet channels, etc.

Fluid flow may be established by any suitable method. For example, external micropumps suitable for pumping small quantities of liquids are available. Micropumps may also be provided in the device itself, driven by thermal gradients, magnetic and/or electric fields, applied pressure, etc. Integration of passively-driven pumping systems and microfluidic channels is described by B. H. Weigl et al., Proceedings of MicroTAS 2000, Enshede, Netherlands, pp. 299-302 (2000).

In some embodiments, fluid flow is established by a gravity flow pump, by capillary action, or by combinations of these methods. A simple gravity flow pump comprises a fluid reservoir either external or internal to the device, which contains fluid at a higher level (with respect to gravity) than the respective device outlet. Such gravity pumps have the deficiency that the hydrostatic head, and hence the flow rate, varies as the height of liquid in the reservoir drops. For many devices, a relatively constant and non-pulsing flow is desired.

To obtain constant flow, a gravity-driven pump as disclosed in published PCT application No. WO 03/008102 A1 (Jan. 18, 2002), herein incorporated by reference, may be used. In such devices, a horizontal reservoir is used in which the fluid moves horizontally, being prevented from collapsing vertically in the reservoir by surface tension and capillary forces between the liquid and reservoir walls. Since the height of liquid remains constant, there is no variation in the hydrostatic head.

Flow may also be induced by capillary action. In such a case, fluid in the respective channel or reservoir will exhibit greater capillary forces with respect to its channel or reservoir walls as compared to the capillary forces in the associated device. This difference in capillary force may be brought about by several methods. For example, the walls of the outlet and inlet channels or reservoirs may have differing hydrophobicity or hydrophilicity. Alternatively, the cross-sectional area of the outlet channel or reservoir is made smaller, thus exhibiting greater capillary force.

In some embodiments, construction of fluidic devices is by soft lithography techniques as described for example by Duffy et al (Analytical Chem 70 4974-4984 1998; See also Anderson et al, Analytical Chem 72 158-64 2000 and Unger et al., Science 288 113-16 2000). Addition-curable RTV-2 silicone elastomers such as SYLGARD 184, Dow Corning Co can be used for this purpose. The dimensions of the channels are readily determined by volume and flow rate properties etc.

The substrate may be of one layer or plurality of layers. The individual layers may be prepared by numerous techniques including laser ablation, plasma etching, wet chemical methods, injection molding, press molding, etc. Casting from curable silicone is most preferred, particularly when optical properties are important. Generation of the negative mold can be made by numerous methods all of which are well known to those skilled in the art. The silicone is then poured onto the mold degassed if necessary or desired and allowed to cure. Adherence of multiple layers to each other may be accomplished by conventional techniques.

A method of manufacture of some devices employs preparing a master through use of negative photoresist SU-8 50 photoresist from Micro Chem Corp Newton Mass.

In some embodiments, devices are injection molded. For example, in some embodiments, devices comprise injection molded thermoplastic fluidic layers.

Figure 3:
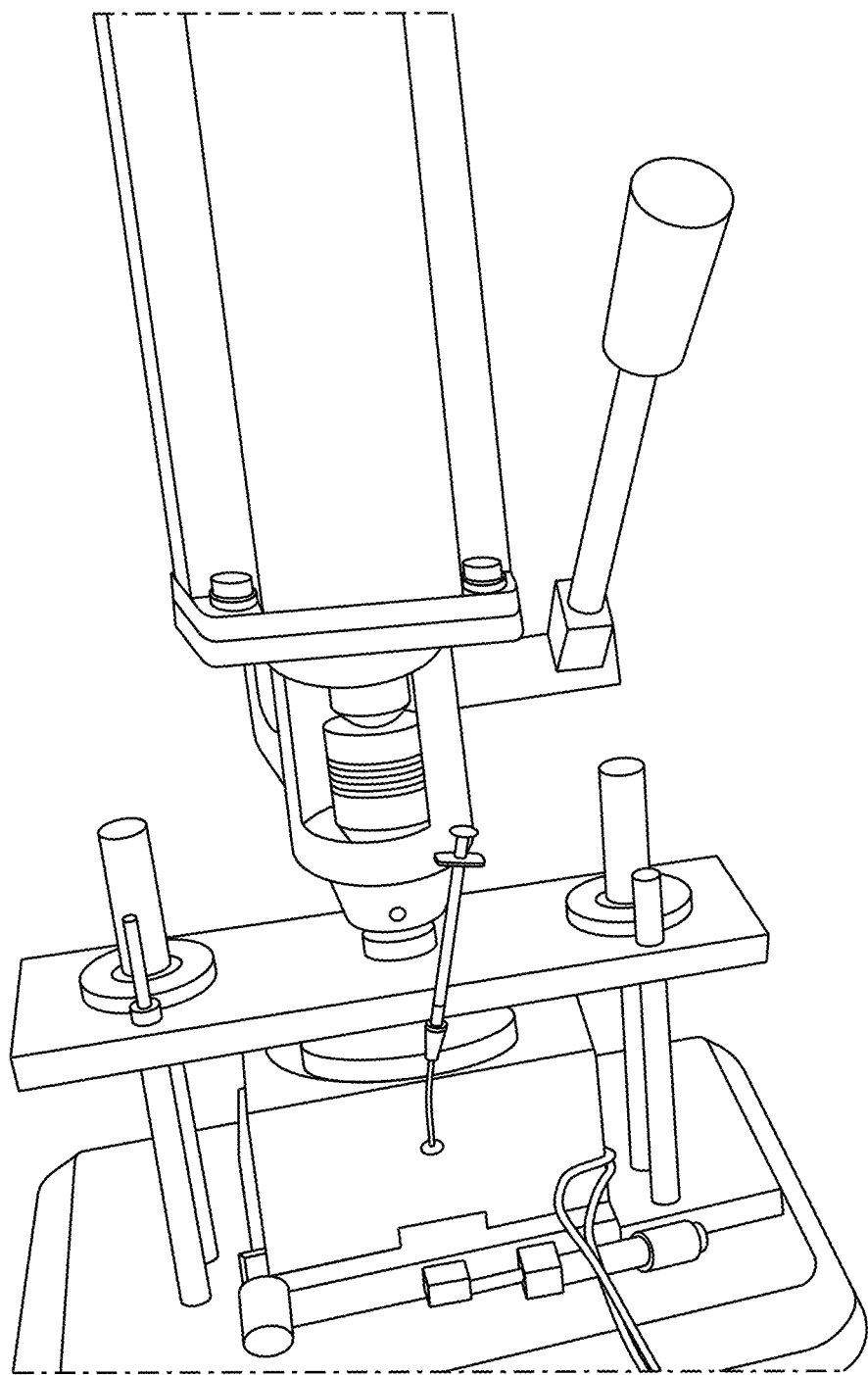
FIG. 3 shows a hemodynamic shearing device (HSD).
Figure 4A:
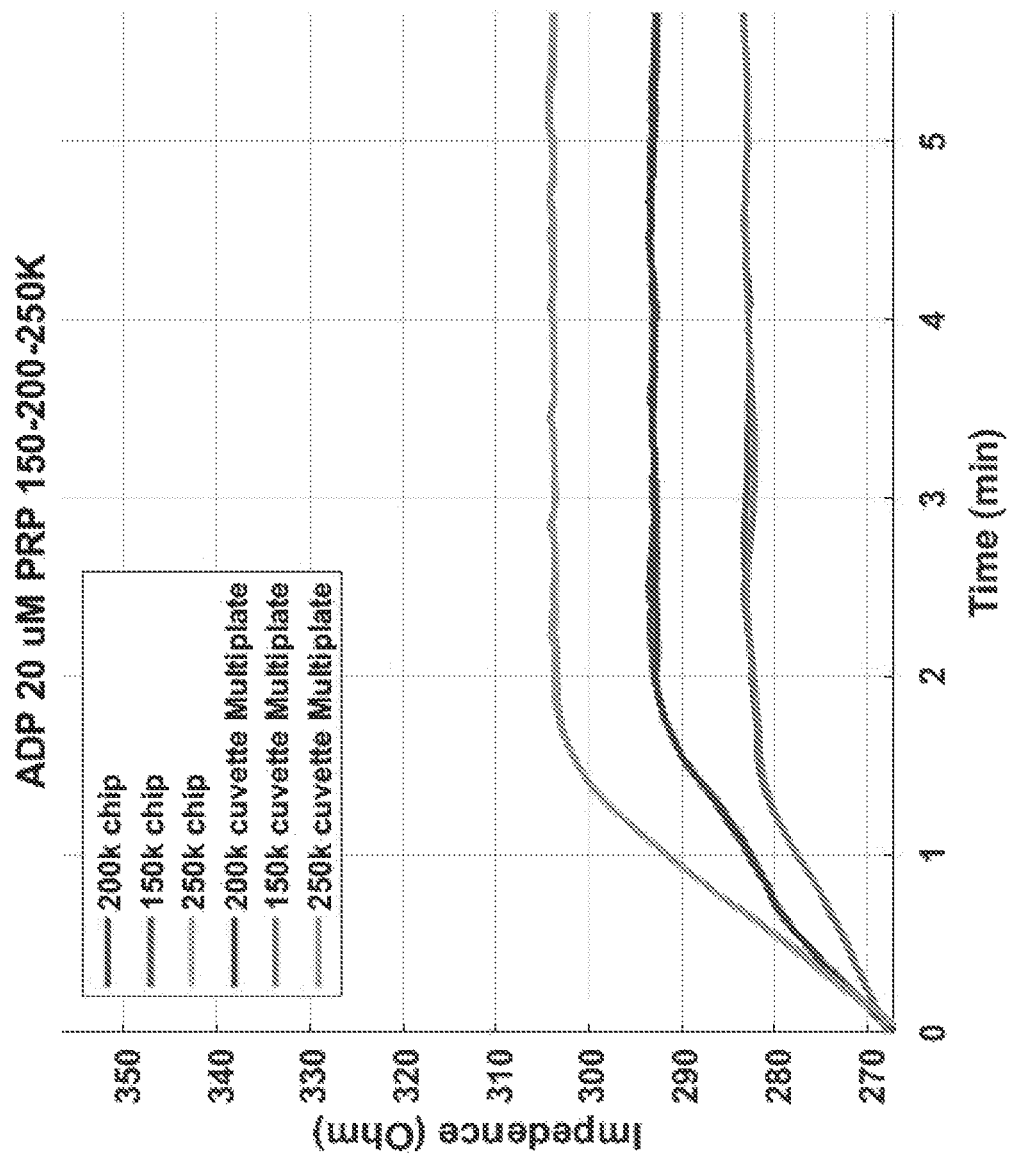
FIG. 4 shows a: ADP 20 uM at different PRP concentration; b: AUC-AU-Slope ADP 10-20 uM at PRP 200000 plt/µl; c: Collagen 20 ug/ml at different PRP concentration; d: AUC-AU-Slope Collagen 10-20 ug/ml at PRP 200000 plt/µl; e: Thrombin 1 U/ml at different PRP concentration; f: AUC-AU-Slope Thrombin 0.1-1 U/ml at PRP 200000 plt/µl; g,h,i: ADP-Collagen-Thrombin AUC-AU-Slope per different donor.
Figure 4B:
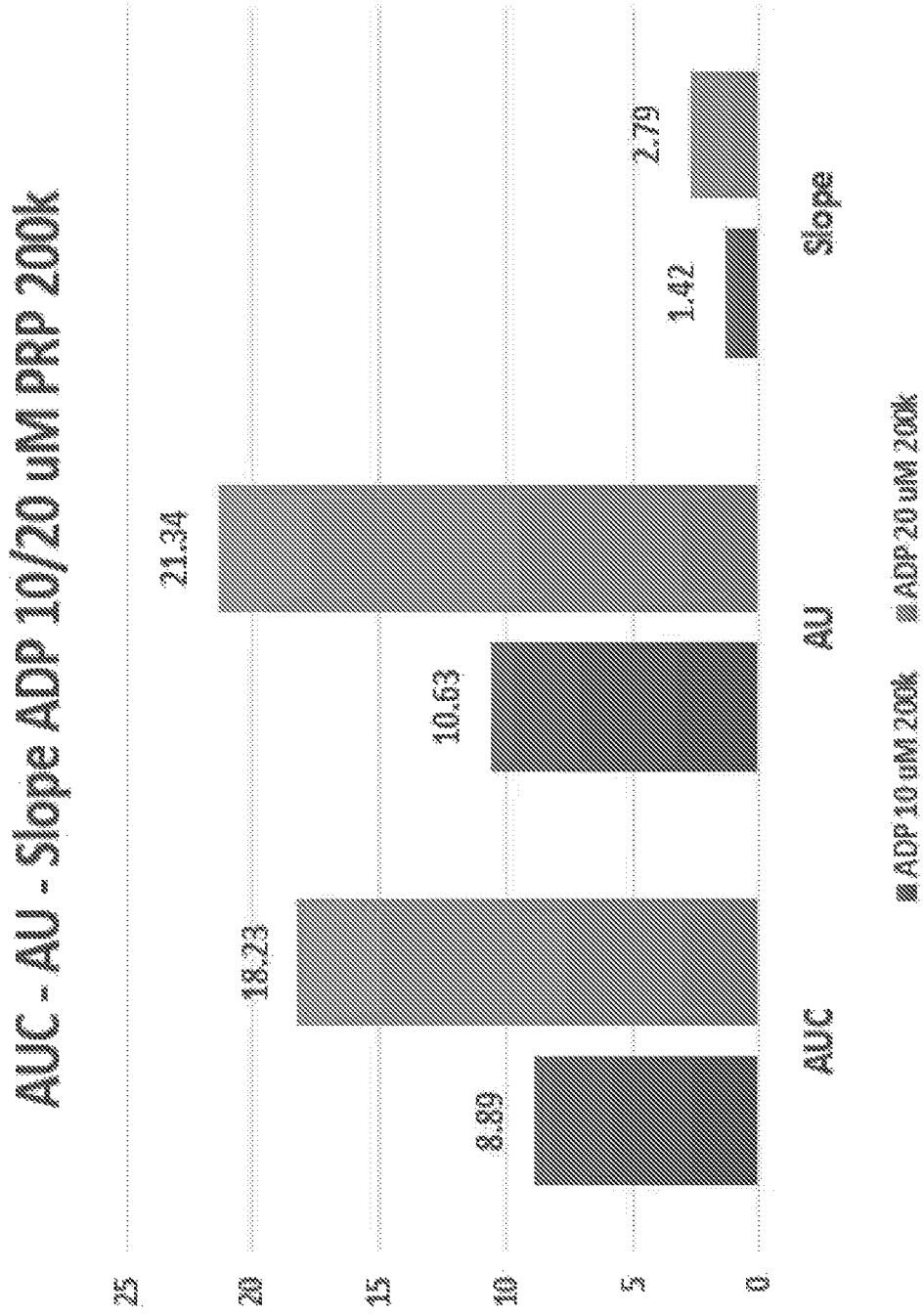
Figure 4C:
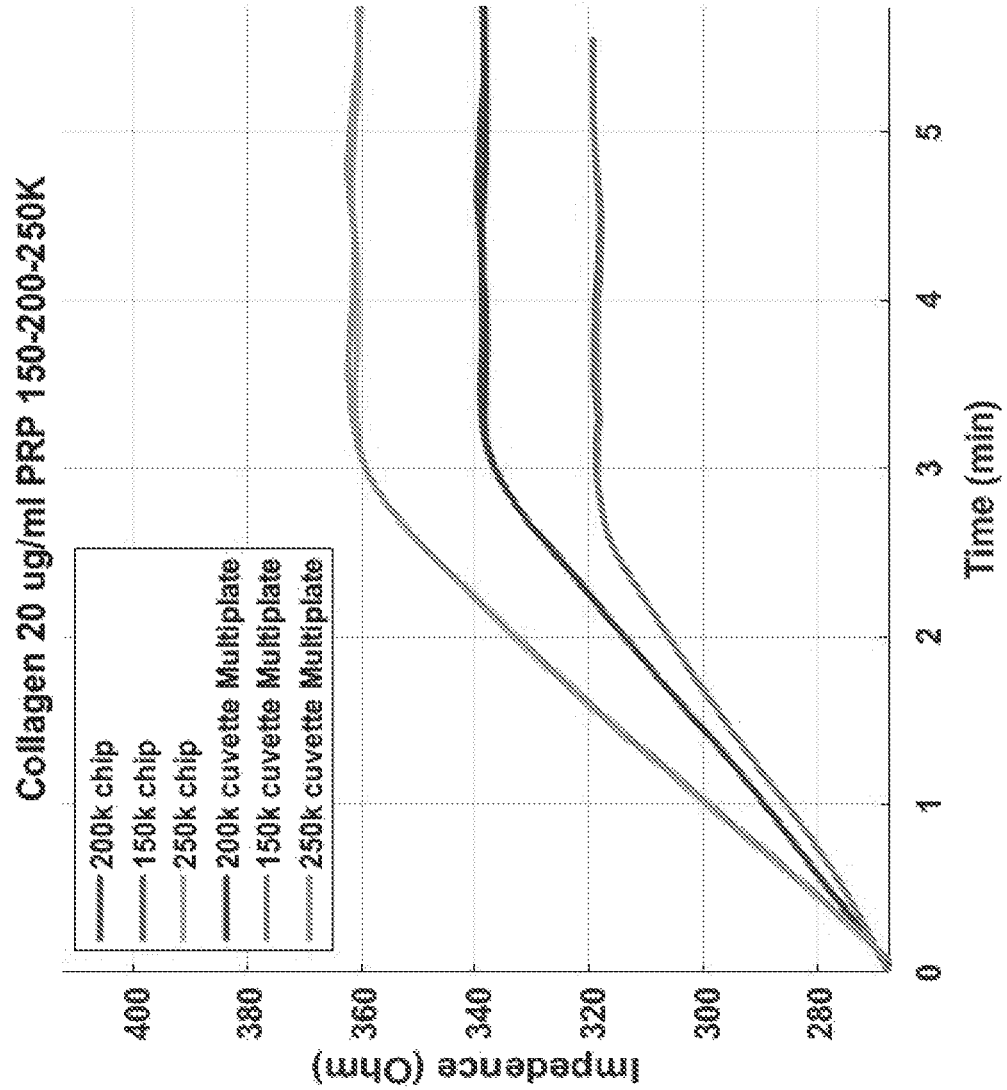
Figure 4D:
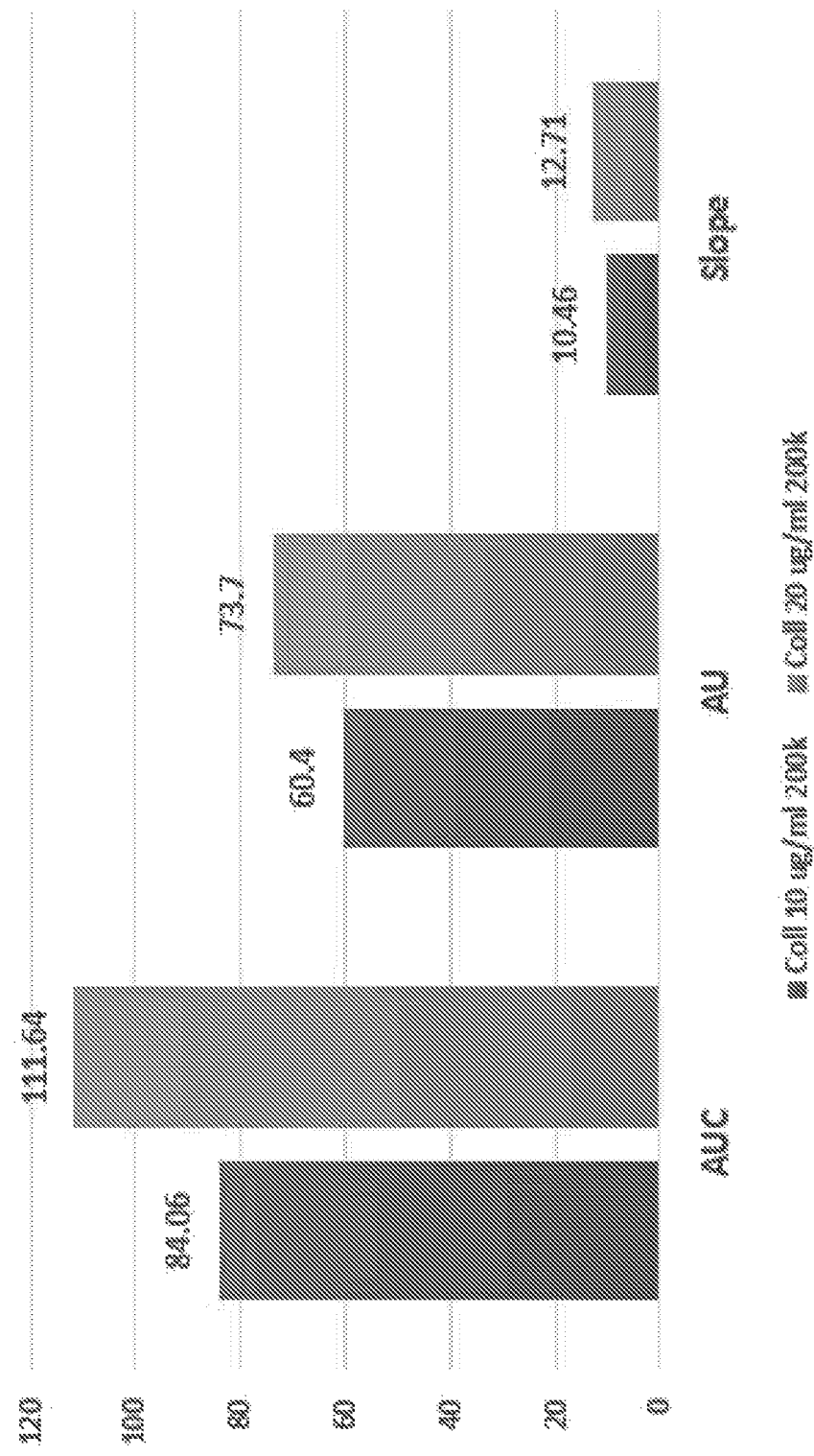
Figure 4E:
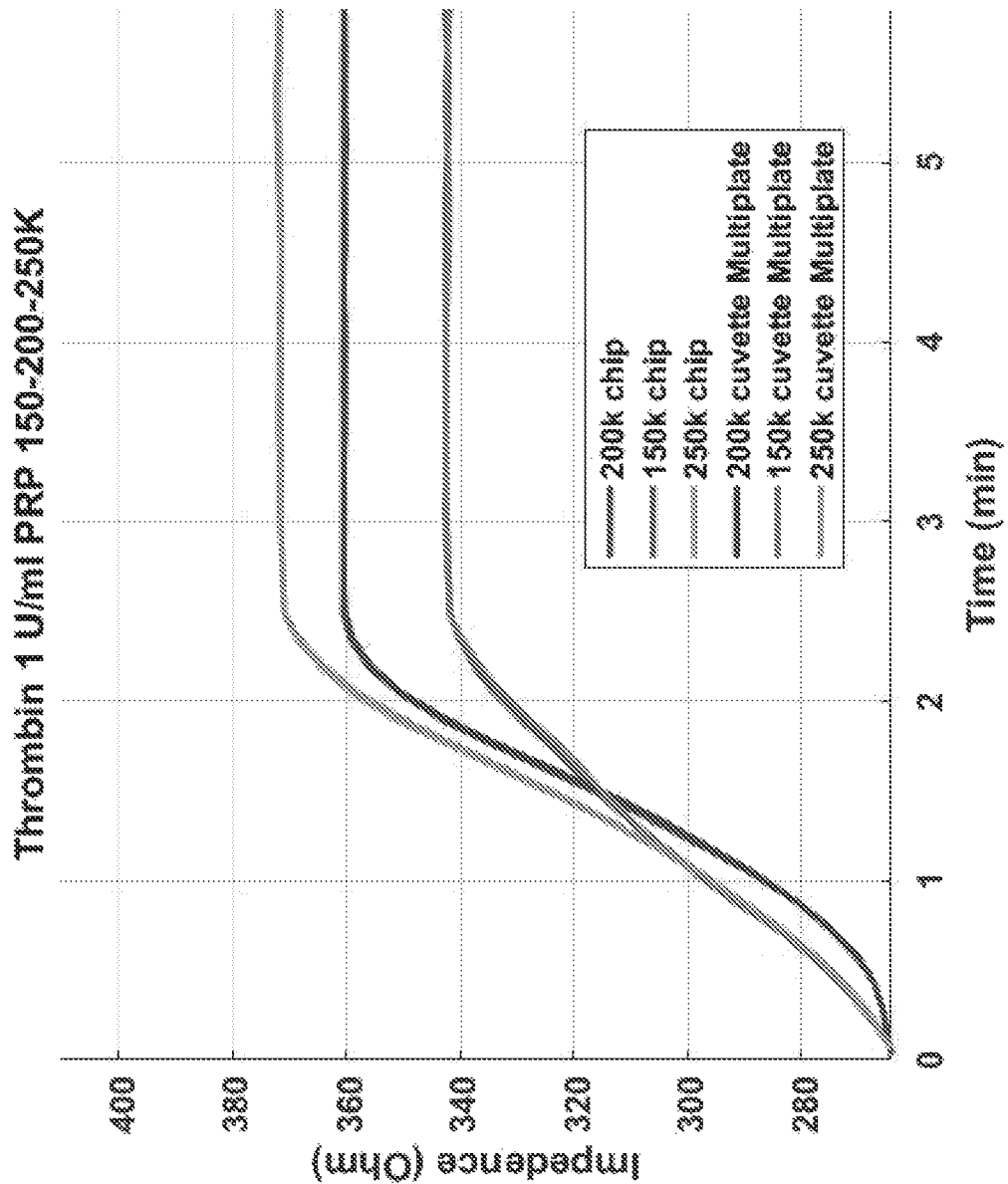
Figure 4F:
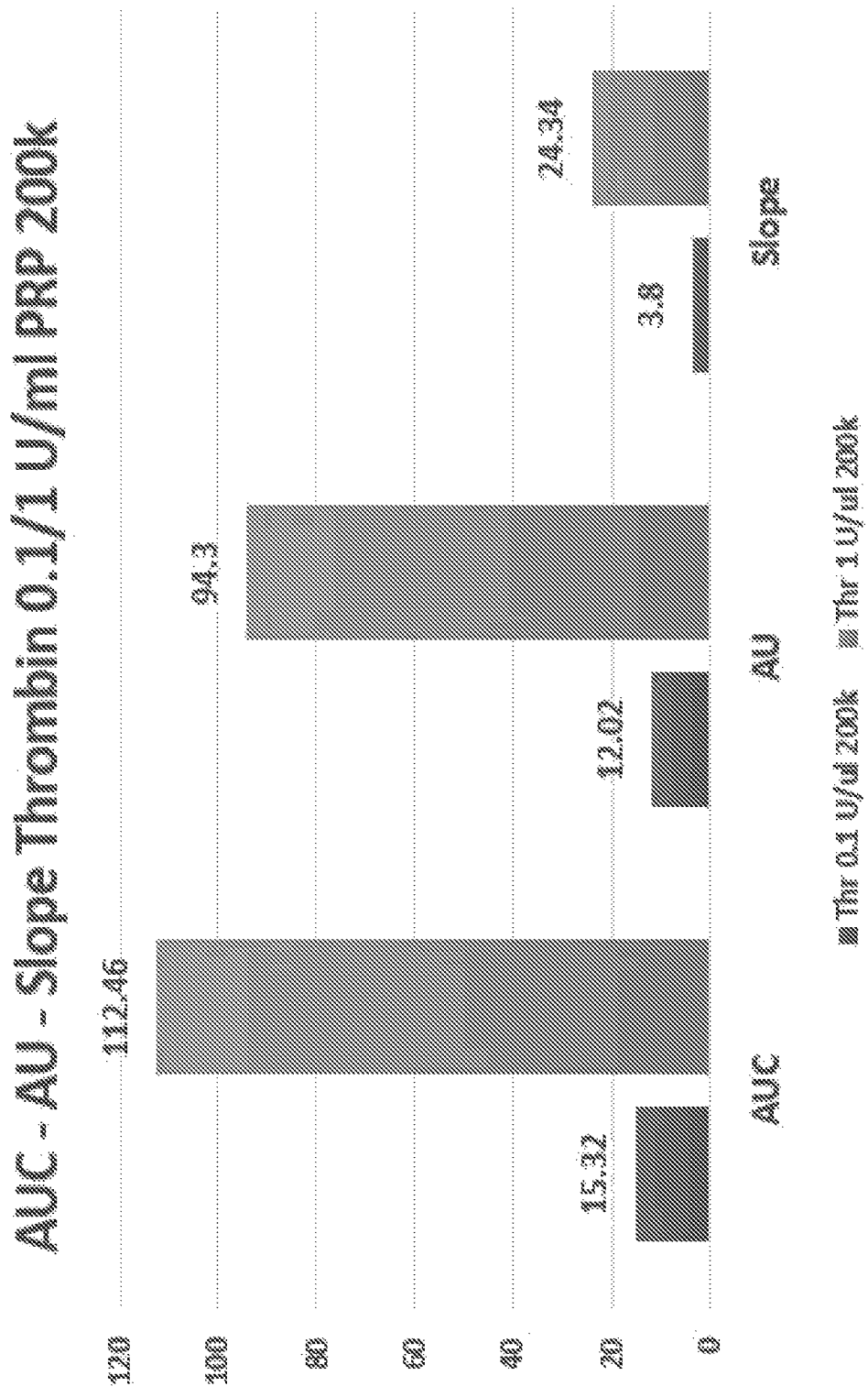
Figure 4G:
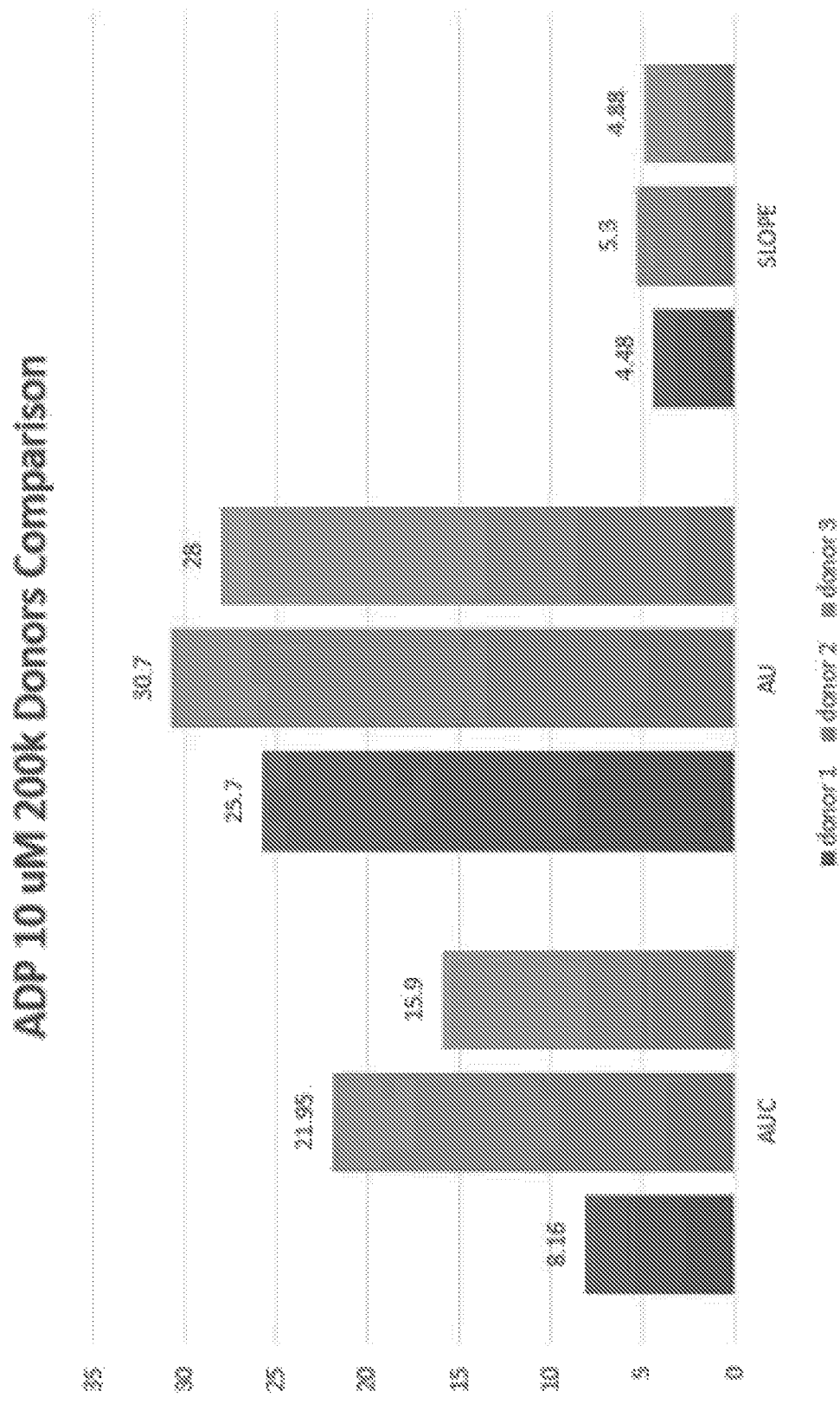
Figure 4H:
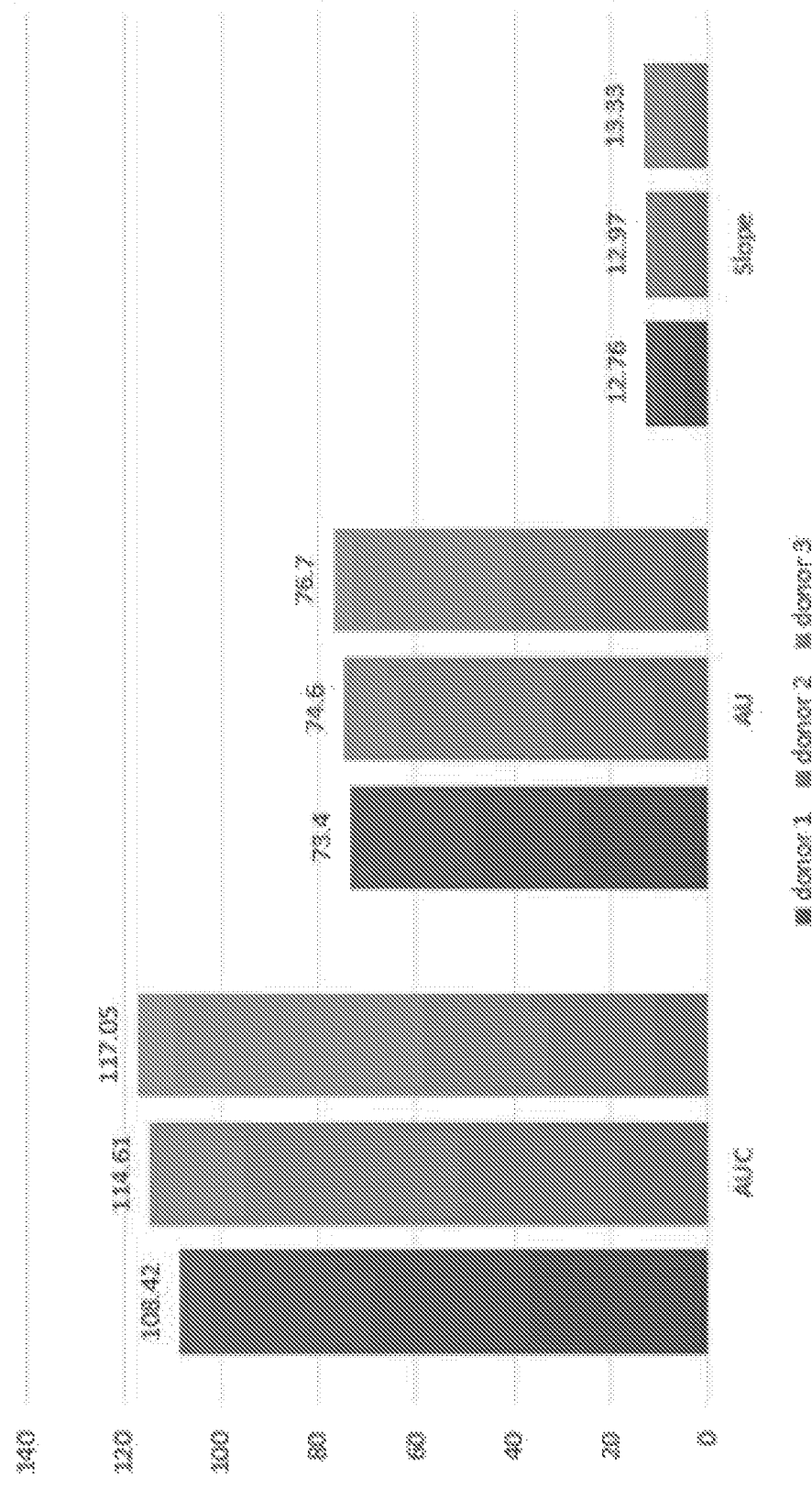
Figure 4I:
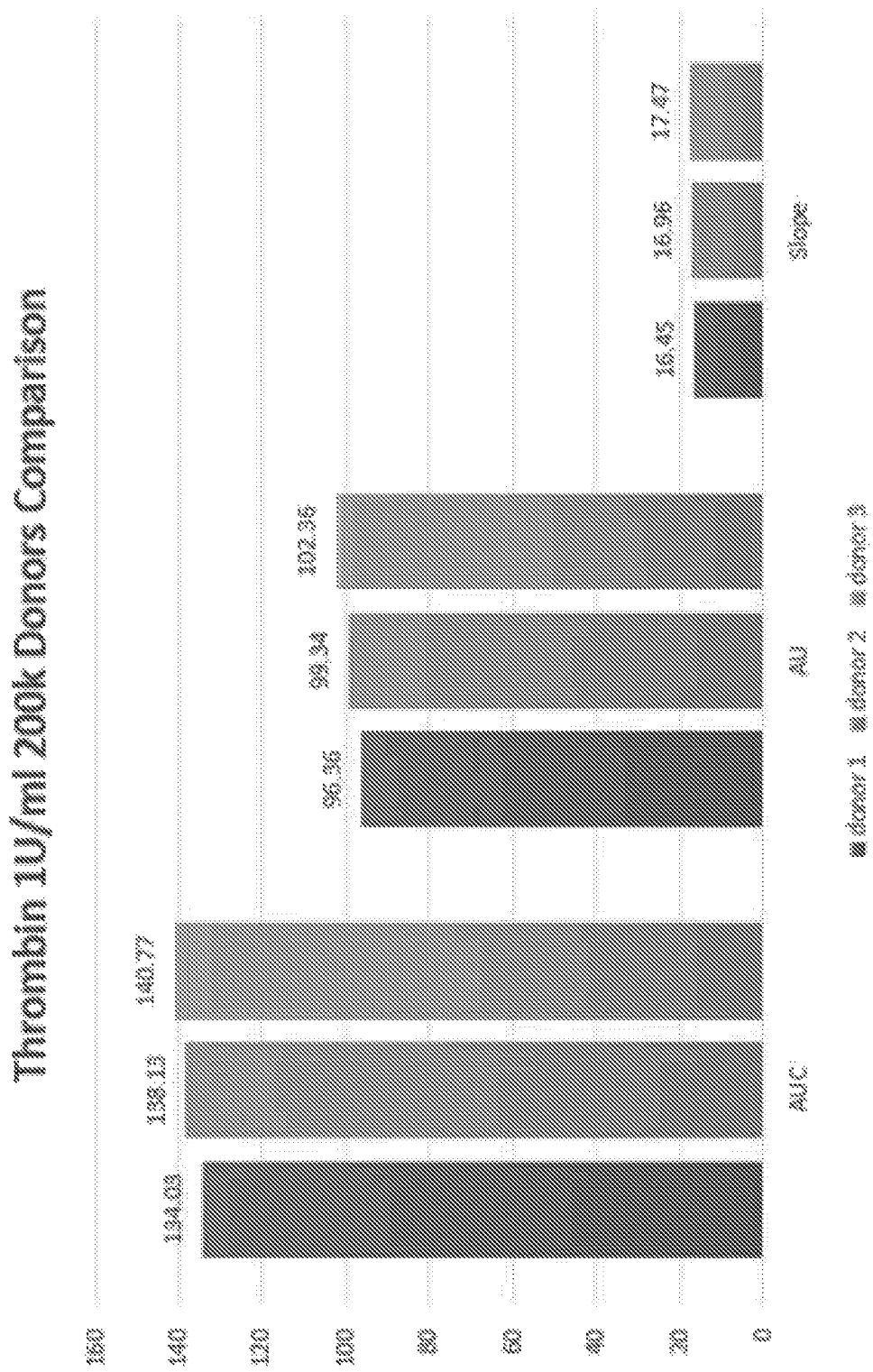
Figure 5A:
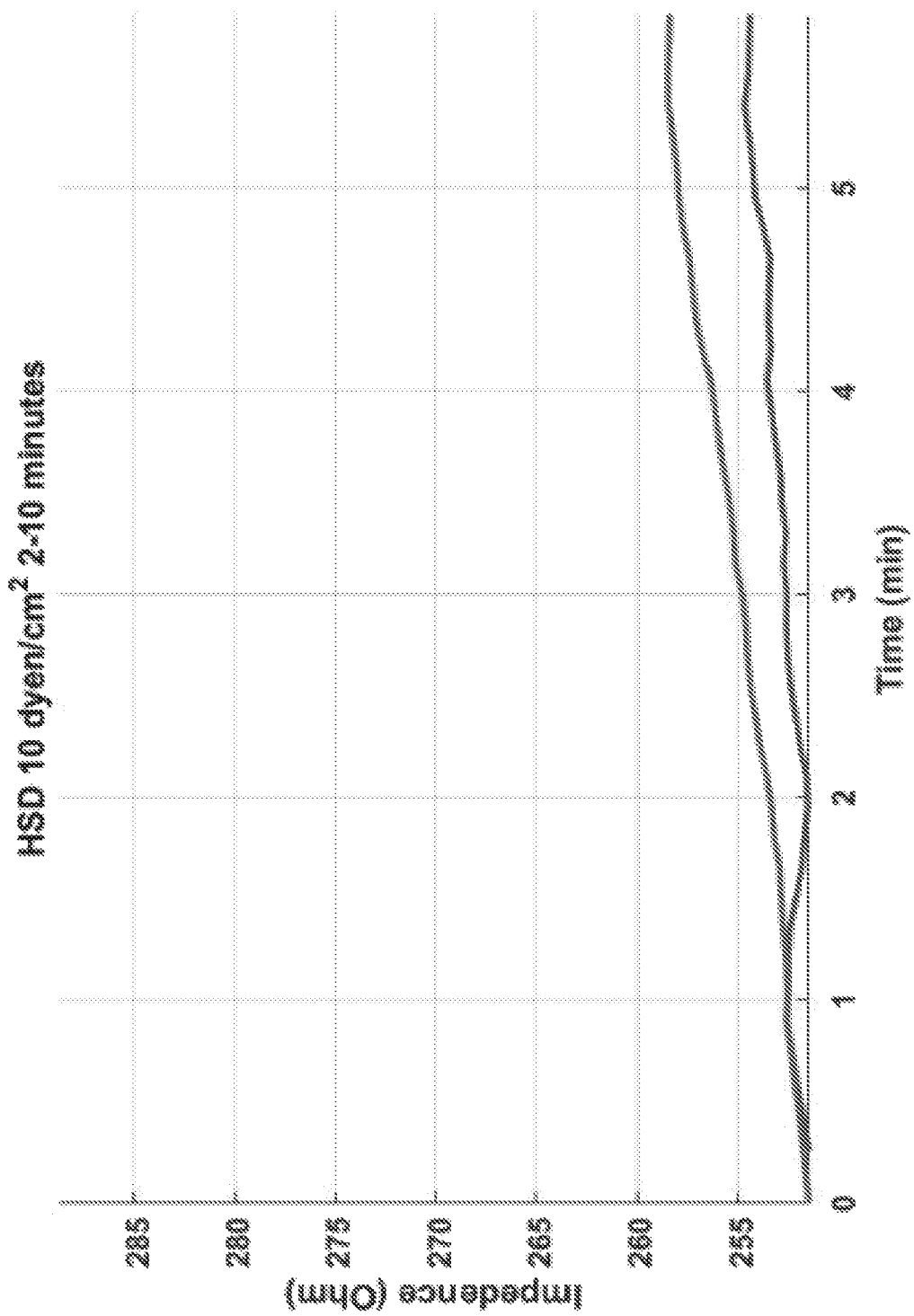
FIG. 5 shows hsd at a: 10 dyne/cm$^2$ at 2 minutes; b: 10 dyne/cm$^2$ 10 minutes; c: 30 dyne/cm$^2$ 2 minutes; d: 30 dyne/cm$^2$ at 10 minutes.
Figure 5B:
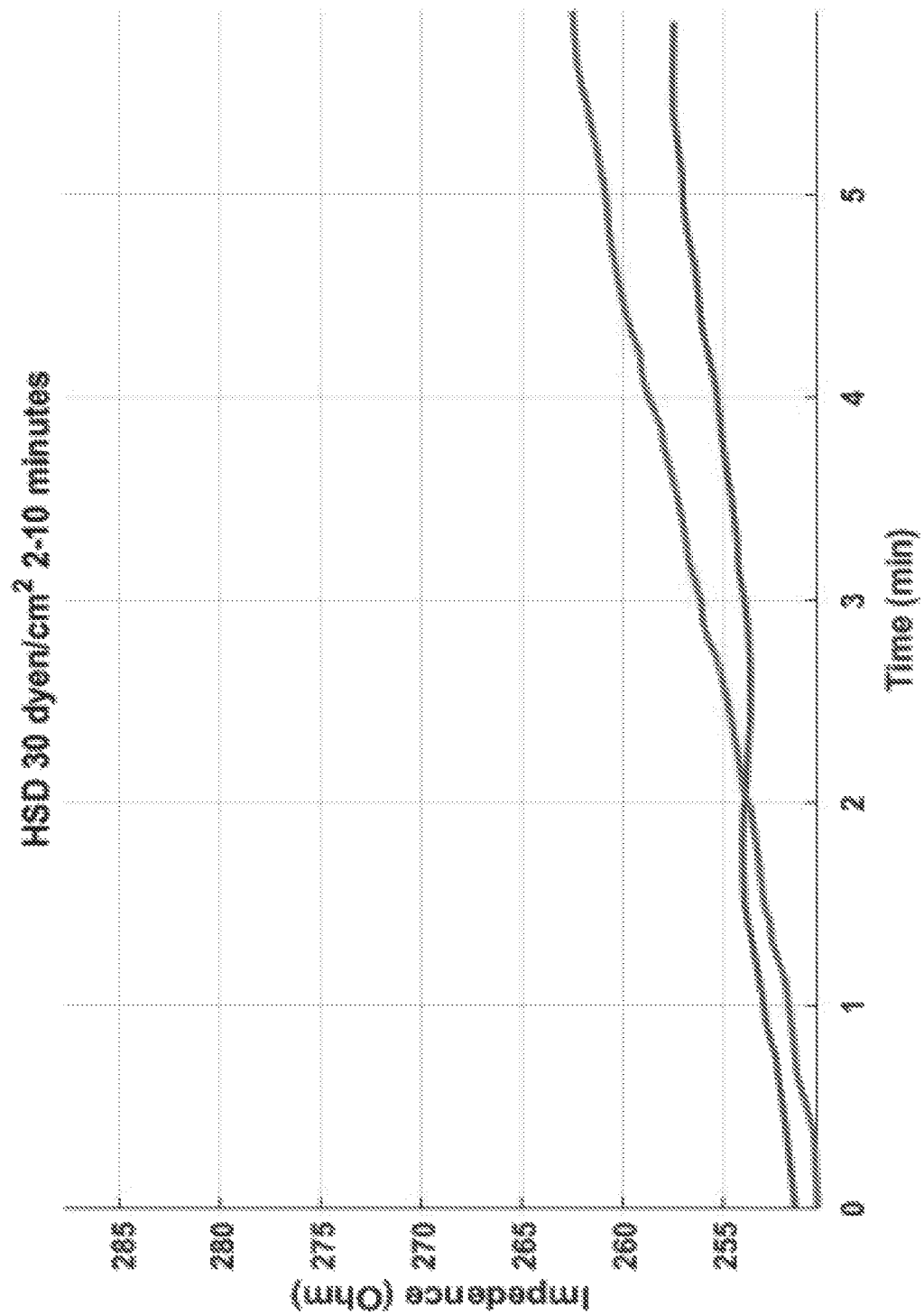
Figure 5C:
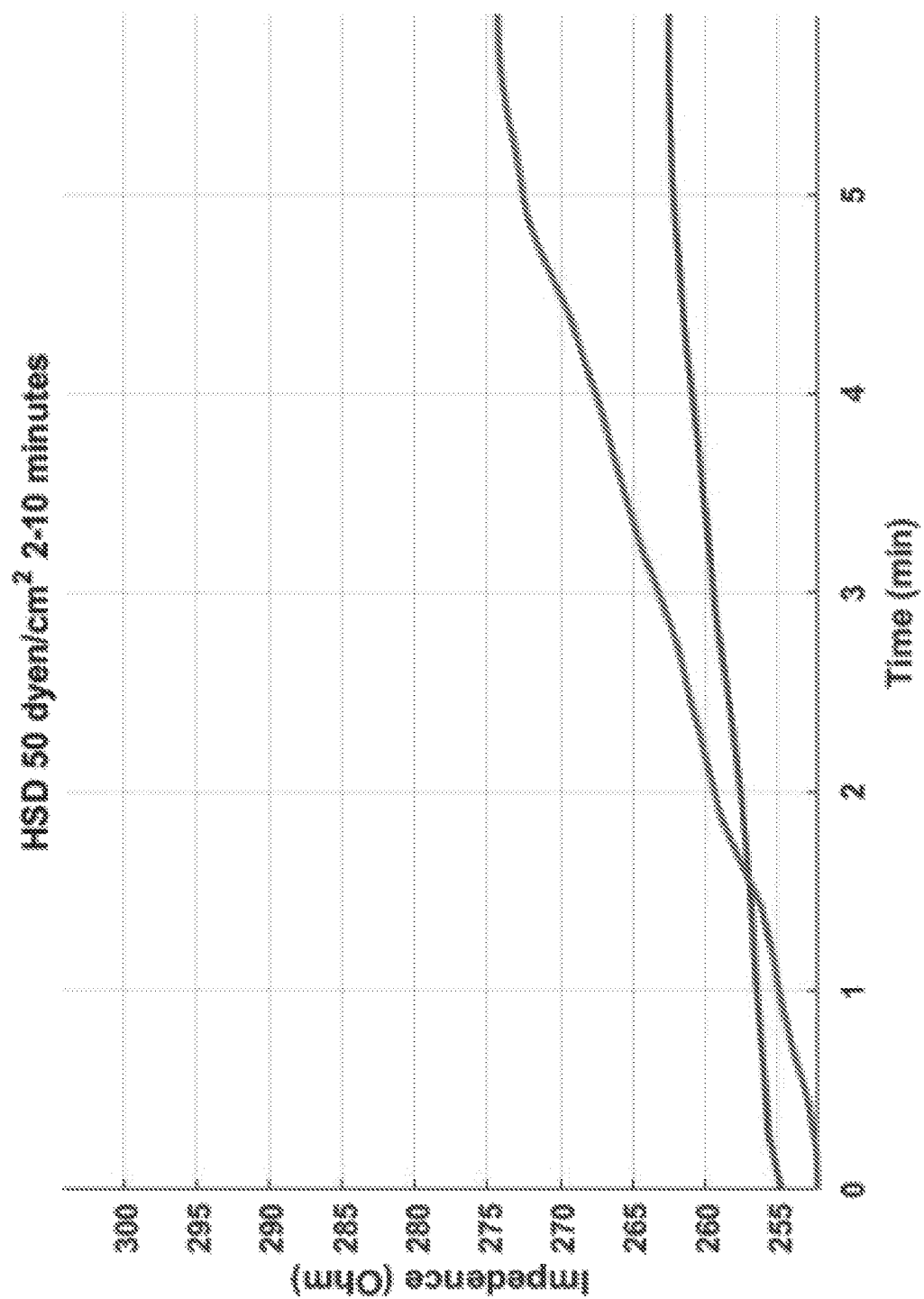
Figure 5D:
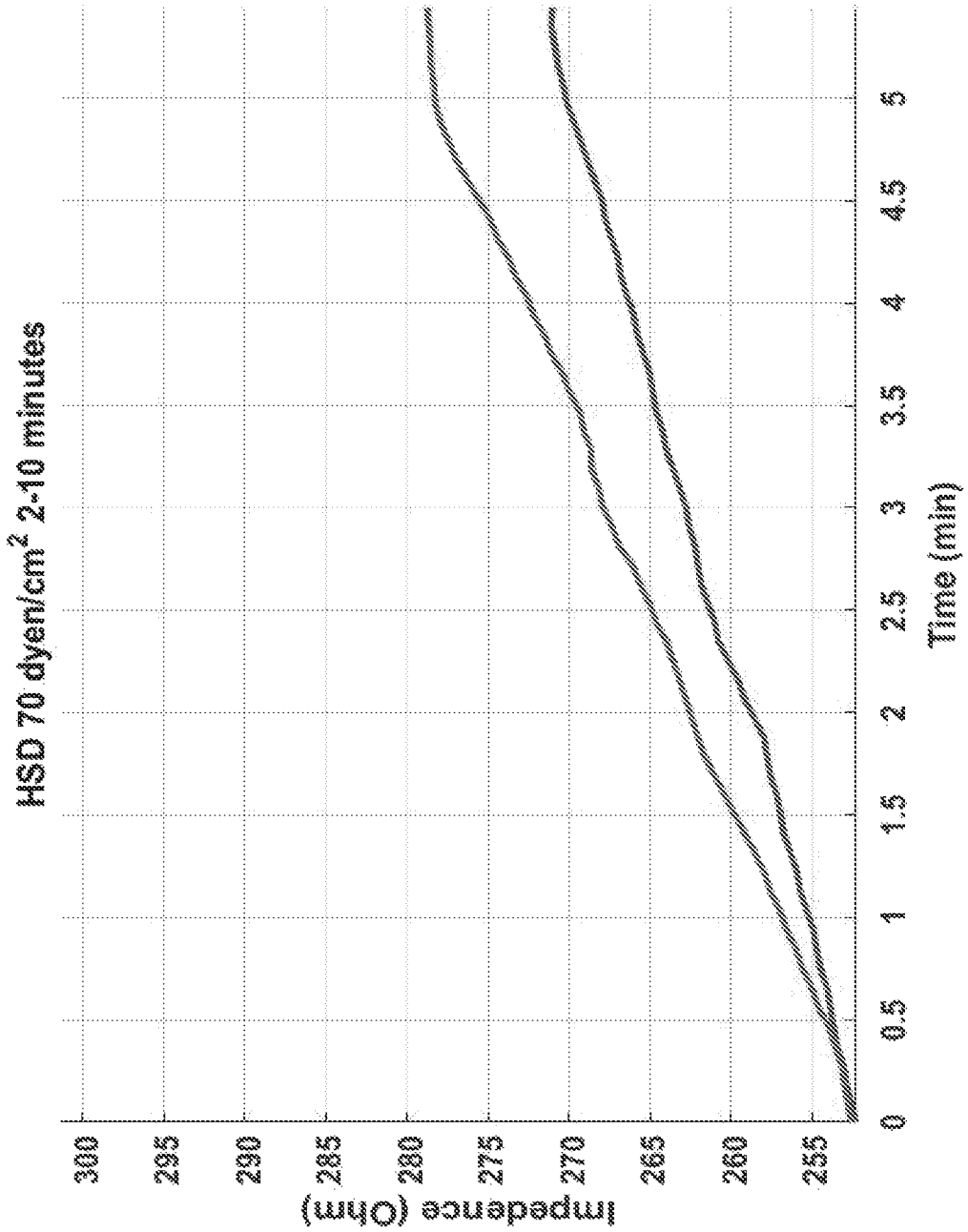

In some embodiments, provided herein are systems comprising the devices described herein and an analysis component configured to measure electrical impedance across the electrodes. In some embodiments, the analysis component comprises a computer processor and computer software and optionally a display component configured to display electrical impedance. In some embodiments, the system further comprises a platelet activation component. The present invention is not limited to particular platelet activation components. Examples include, but are not limited to, calcium chloride and an additional component selected from, for example, a device configured to deliver mechanical stimuli (e.g., a shearing device) and a platelet agonist (e.g., including but not limited to, arachidonic acid, thrombin, adenine di-phosphate (ADP), epinephrine, collagen, or ristocetin). Exemplary shearing devices are shown in FIG. 3, although options for mechanical activation are specifically contemplated.

In some embodiments, a software component is utilized to analyze electrical impedance. For example, in some embodiments, software is configured to process data, determine impedance, and provide a report.

In some embodiments, a computer-based analysis program is used to translate the raw data generated by the detection assay (e.g., impedance) into data of predictive value for a clinician (e.g., choice of therapy). The clinician can access the predictive data using any suitable means. Thus, in some preferred embodiments, the present disclosure provides the further benefit that the clinician, who is not likely to be trained in molecular biology, need not understand the raw data. The data is presented directly to the clinician in its most useful form. The clinician is then able to immediately utilize the information in order to optimize the care of the subject.

The present disclosure contemplates any method capable of receiving, processing, and transmitting the information to and from laboratories conducting the assays, information provides, medical personal, and subjects. For example, in some embodiments of the present disclosure, a sample (e.g., blood or platelet rich plasma) is obtained from a subject and submitted to a profiling service (e.g., clinical lab at a medical facility, profiling business, etc.), located in any part of the world (e.g., in a country different than the country where the subject resides or where the information is ultimately used) to generate raw data. Once received by the profiling service, the sample is processed and a profile is produced (e.g., impedance), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of heart attack or need for change in treatment) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention or counseling based on the results. In some embodiments, the data is used for research use. For example, the data may be used to screen new anti-coagulation or coagulation drugs.

In some embodiments, systems comprising devices, detectors, software, and computer components (e.g., computer processor and display screen, smart phone, etc.) are provided. In some embodiments, the detection and analysis components are provided as a platform and the devices are provided as cartridges or plates (e.g., disposable or re-usable devices). For example, in some embodiments, the portion of the system that contacts patient sample is provided as a disposable microfluidics device and the analysis platform is a stand-alone reusable component that can accept and analyze cartridges specific for one or more target antigens.

II. Methods

Provided herein are research, screening (e.g., drug screening), and clinical applications of the systems and devices described herein. In some embodiments, provided herein are methods of measuring platelet aggregometry, comprising: a) contacting a sample comprising blood or blood product comprising platelets (e.g., platelet rich plasma) with the chamber of a system as described herein; b) activating the platelets using the platelet activation component; and c) measuring electrical impedance across the electrodes. In some embodiments, the $CaCl_2$ and agonist is inserted into the chamber of the device using the inflow channels. In some embodiments, the sample is from a subject (e.g., a subject undergoing anti-coagulation therapy, a subject with heart disease, a subject undergoing a myocardial infarction, a subject with peripheral artery disease, a subject with limb ischemia, a subject with pulmonary emboli, or a subject with cancer). In some embodiments, the method further comprises the step of contacting the sample with a test compound (e.g., an anti-coagulation agent or a coagulation agent). In some embodiments, the contacting is in the chamber of the device. In some embodiments, the method is repeated over time on a subject undergoing treatment for a disease or condition. In some embodiments, the impedance results are used to determine or alter a treatment course of action (e.g., anti-coagulation therapy). In some embodiments, the anti-coagulation therapy is aspirin or clopidogrel.

EXPERIMENTAL

The following examples are provided in order to demonstrate and further illustrate certain preferred embodiments and aspects of the present invention and are not to be construed as limiting the scope thereof.

Example 1

Experiments were conducted that verified and validated the efficacy of the device system. First, aggregation with this system was compared to that of the current laboratory standard of impedance aggregometry—the Multiplate system. In these comparative studies, PRP and standard platelet agonists were utilized e.g., ADP, collagen and thrombin. Second, the reproducibility was examined for both systems. Third, PRP samples were processed under shear stress condition in order to activate platelets using mechanical stimuli instead of chemical agents as an agonist. The aggregates were examined microscopically comparing MICELI vs standard electrical or optical aggregometry, to compare the morphology of the obtained thrombus.

The chip was tested using the same work protocol as the Multiplate system in order to compare the results. The experimental protocol was: 1) use of a saline solution for platelets like $CaCl_2$; 2) use of a chemical agonist to stimulate platelet to aggregate; 3) measurement timing of 9 minutes divided in 3 minutes of incubation of PRP (Platelets Rich Plasma) with only $CaCl_2$ 1 mM and after this, the addition of the agonist with 6 minutes of measurement. In order to have a good trend of data for the validation and to verify the reproducibility of the results, three agonists were used: ADP, Collagen and Thrombin.

In order to verify the sensitivity of the device every experiment was replicated for each agonist with 3 different healthy male donors.

Next, aggregometry tests were performed using activated platelets in shear stress condition. Shear stress is a utilized way to activate platelets. To perform the activation, a modified cone plate viscometer, the Hemodynamic Shearing Device (HSD) was. This devices is a cylindrical cone inserted in a plate with a cylindrical space (FIG. 3). The two parts are not in contact with each other but there is a layer hosting the sample solution of PRP (¾ ml). The rotation of the cone with respect to the fixed plate translates into a shear stress, which activates platelets. Typically, shear stresses are varied in the range 10-30-50-70 dyne/cm$^2$.

To perform the impedance measurements a commercial device named RedPitaya® able to work like an Impedance Analyzer was used.

Agonist Experiments

The agonists used for these experiments were ADP, Collagen and Thrombin at different concentration and on three different healthy male donors. The concentration of platelets in PRP was tested at 150000-200000-250000 plt/µl. To compare and analyze the results three parameters were used in the aggregometry test, namely the Area Under the Curve (AUC), the Aggregation Unit (AU) and the Slope of The Curve (Slope). The agonists used were:

ADP: 2 different concentrations were used, 20 µM (the most common concentration used in the aggregometry experiments in literature) and 10 µM. Results are provided in FIG. 4, a-b) together with the AUC, AU and Slope parameters.

Collagen: 2 different concentrations were used, 10 µg/ml and 20 µg/ml (FIG. 4, c-d).

Thrombin: 2 different concentrations were used, 0.1 U/ml and 1 U/ml (the most common concentration used in the aggregometry experiments in literature). Clear evidence of the different effect of the two concentrations is shown in FIG. 4, e-f.

FIG. 4 shows a AUC-AU-Slope comparison for each agonist which was tested on three donors.

Shear Stress Experiments

These experiments were performed using the standard concentration of PRP at 200000 plt/µl and $CaCl_2$ at the standard concentration of 1 mM. The collection of the sample and measurements were done after 2 and 10 minutes to estimate the aggregation after a minimum and maximum activation time (FIG. 5, a-b-c-d).

Figure 6:
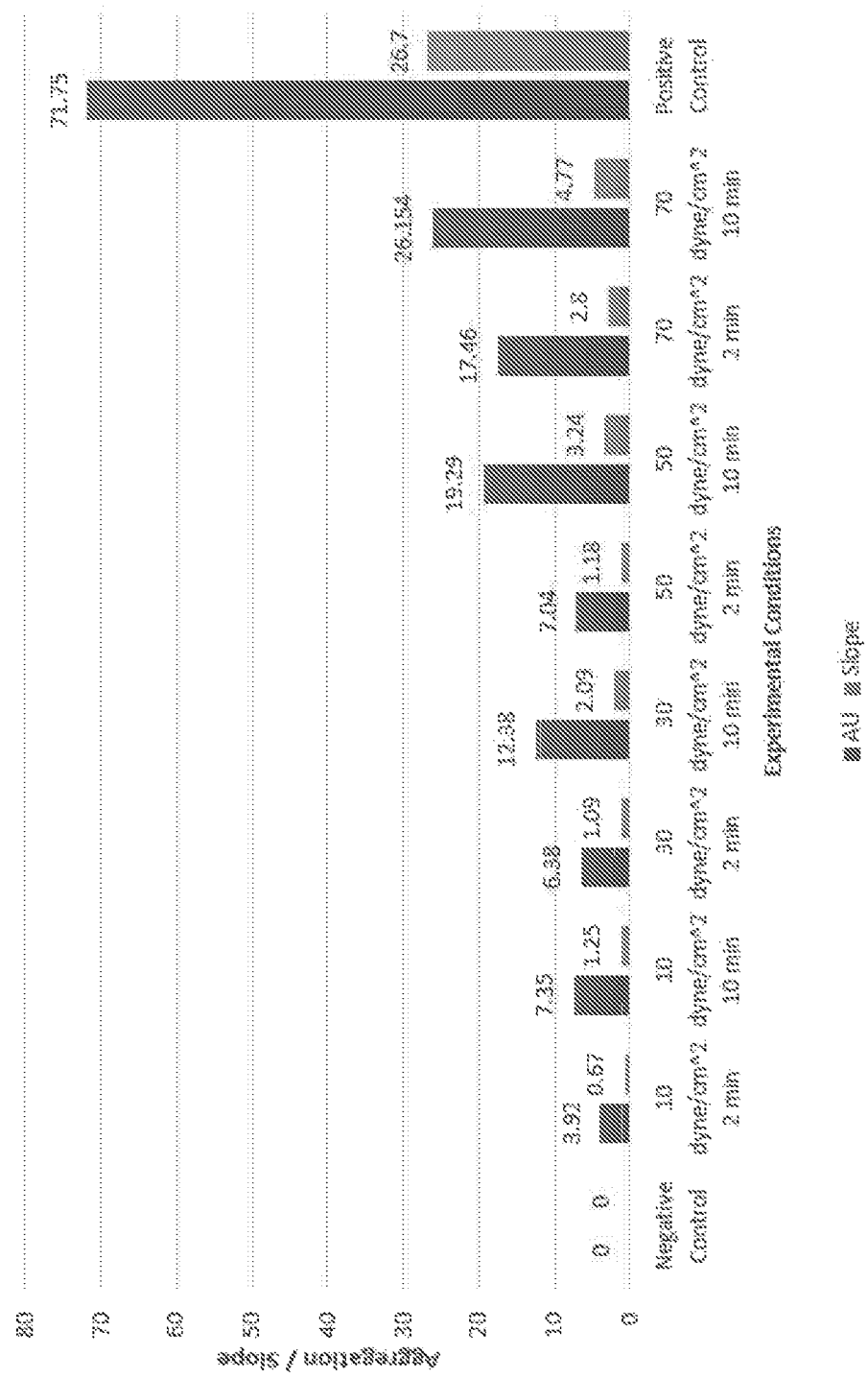
FIG. 6 shows histograms AU and Slope data by hsd at 10 dyne/cm$^2$ at 2-10 minutes; 30 dyne/cm$^2$ at 2-10 minutes; 50 dyne/cm$^2$ at 2-10 minutes; 70 dyne/cm$^2$ at 2-10 minutes.

10 dyne/cm$^2$:
30 dyne/cm$^2$:
50 dyne/cm$^2$:
70 dyne/cm$^2$:

FIG. 5 shows a comparison of the AU and Slope results of the shear stress conditions with the different HSD setting with two controls, a negative control considering not-activated platelets with $CaCl_2$ and a positive considering platelet aggregation in the Collagen 20 µg/ml like agonist condition (FIG. 6).

The results of the standard aggregometry tests using a chemical agonist like "activator" clearly show that the device described herein is suitable for impedance measurements.

Starting from ADP effect analysis, it is possible to observe the difference in terms of AUC, AU and Slope. This difference is statistically significant with the expected results according to the different concentrations used. The results show the change in impedance values from 10 µM to 20 µM. Results shows the velocity with which the agonist is able to influence platelets.

With Collagen and Thrombin, a data difference linked to the different agonist concentration was observed.

Comparing the data (AUC, AU and Slope) and the curves of the tree different agonist for each condition it was noted that the device was sensitive to the different agonists. One agonist can have chemical properties and effects totally different than others, for example ADP is known to be one of the weakest agonist while Collagen and Thrombin are among the strongest agonists.

An influence of the PRP concentration in the aggregometry test was also observed. There was a clear difference between a sample at 150000 plt/µl and a sample at 200000 plt/µl or 250000 plt/µl. It is contemplated that a higher platelet concentration leads to higher aggregation because platelets are closer to each other.

A validation was performed comparing all these results with a commercially available Multiplate Electronic Aggregometer system. There was a clear matching between the 2 systems.

In the case of platelets activated with shear stress the resulting aggregation is less than the aggregation with agonist. There was an escalation of values from 10 to 70 dyne/cm$^2$ due to different activation levels.

The difference between the three donors was present but statistically acceptable ($P<0.05$). In particular, the donor presenting the highest platelet concentration demonstrated the highest aggregation values.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A microfluidic device, comprising:
an assay chamber comprising two electrodes that bridge said assay chamber; and first and second inflow channels with a cross-section narrower than the cross section of said assay chamber in fluid communication with said assay chamber, wherein said first and second inflow channels are oriented perpendicularly to said electrodes and are separated from each other by 180 degrees, and wherein said electrodes and/or said chamber is coated with a protein selected from the group consisting of fibrinogen, fibrin, collagen, vitronectin, and laminin.

2. The device of claim 1, wherein said plurality of inflow channels comprises two distinct channels.

3. The device of claim 1, wherein said electrodes are not in operable communication with said plurality of inflow channels.

4. The device of claim 3, wherein said electrodes are oriented perpendicular to said plurality of inflow channels.

5. The device of claim 1, wherein said chamber is round.

6. The device of claim 1, wherein said plurality of inflow channels comprises two channels separated by 180 degrees.

7. The device of claim 1, wherein said device is portable.

8. A system, comprising:
a) a device comprising an assay chamber comprising two electrodes that bridge said assay chamber; and first and second inflow channels with a cross-section narrower than the cross section of said assay chamber in fluid communication with said assay chamber, wherein said first and second inflow channels are oriented perpendicularly to said electrodes and are separated from each other by 180 degrees, and wherein said electrodes are coated with a protein selected from the group consisting of fibrinogen, fibrin, collagen, vitronectin, and laminin; and
b) an analysis component configured to measure electrical impedance across said electrodes.

9. The system of claim 8, wherein said analysis component comprises a computer processor and computer software.

10. The system of claim 8, wherein said analysis component further comprises a display component configured to display electrical impedance.

11. The system of claim 8, wherein said system further comprises a platelet activation component.

12. The system of claim 11, wherein said platelet activation component is calcium chloride and an additional component selected from the group consisting of a device configured to deliver mechanical stimuli and a platelet agonist.

13. The system of claim 12, wherein said platelet agonist is selected from the group consisting of arachidonic acid, thrombin, adenine di-phosphate (ADP), thrombin receptor agonist peptide (TRAP), epinephrine, collagen, and ristocetin.

14. The system of claim 12, wherein said device configured to deliver mechanical stimuli is a shearing device.

15. A method of measuring platelet aggregometry, comprising:
a) contacting a sample comprising blood or blood product comprising platelets with the chamber of the system of claim 8;
b) activating said platelets using a platelet activation component; and
c) measuring electrical impedance across said electrodes.

16. The method of claim 15, wherein said blood product is platelet rich plasma.

17. The method of claim 15, further comprising the step of contacting said sample with a test compound.

18. The method of claim 17, wherein said test compound is an anti-thrombotic, anti-platelet, anti-coagulation, thrombotic, platelet activating, or coagulation agent.

19. The device of claim 1, wherein said assay chamber is coated with a protein selected from the group consisting of fibrinogen, fibrin, collagens, vitronectin, and laminin.

* * * * *